United States Patent [19]

Matsumoto et al.

[11] 4,245,127
[45] Jan. 13, 1981

[54] PROCESS FOR CHLORINATING XYLENOLS

[75] Inventors: Teiziro Matsumoto; Moriyasu Matsuda; Hiroshi Mizokami; Tsuneo Kibamoto; Katsuma Hatta, all of Kakogawa, Japan

[73] Assignee: Seitetsu Kagaku Co., Ltd., Hyogo, Japan

[21] Appl. No.: 736,029

[22] Filed: Oct. 27, 1976

[30] Foreign Application Priority Data

Oct. 31, 1975 [JP] Japan .................. 50-131685

[51] Int. Cl.$^3$ .............................................. C07C 39/27
[52] U.S. Cl. ................................................... 568/779
[58] Field of Search ........... 260/623 H, 623 R, 621 R; 568/779

[56] References Cited

U.S. PATENT DOCUMENTS 3,542,882  11/1970  Ashall et al. .................. 260/623 H
3,920,757  11/1975  Watson .......................... 260/623 H

FOREIGN PATENT DOCUMENTS 948601  5/1963  United Kingdom ..................... 260/623

Primary Examiner—Werren B. Lone
Attorney, Agent, or Firm—Pollock, Vande Sande and Priddy

[57] ABSTRACT

Chlorination of xylenols with a chlorinating agent such as sulfuryl chloride in the presence of a metal chloride catalyst is conducted in further presence of 0.001 to 1% by weight of a sulfur compound, based on the xylenols, whereby industrially useful xylenols are obtained safely with a high selectivity and high yield.

7 Claims, No Drawings

PROCESS FOR CHLORINATING XYLENOLS

This invention relates to an improved process for chlorinating xylenols, and more particularly to an improved process for chlorinating xylenols, wherein xylenols are chlorinated by adding 0.01 to 10% by weight of a metal chloride as a catalyst to the xylenols, on the basis on the weight of xylenols, and carrying out chlorination of the xylenols in the presence of a chlorinating agent, characterized by adding 0.0001 to 1% by weight of at least one of sulfur compounds to said reaction system, on the basis of the weight of xylenols.

Chlorinated xylenols are industrially important compounds as antibacterial and antifungal agent, agricultural chemicals and their intermediates. The chlorinated xylenols resulting from chlorination of xylenols have various isomers, and p-chloroxylenols are much more useful than other isomers such as o-chloroxylenols. It is a great task in the chlorination on an industrial scale to improve a selectivity to p-chloro isomers.

An object of the present invention is to provide and industrially useful, improved process for producing p-chloroxylenols by chlorinating xylenols with high selectivities to p-chloroxylenols in high yields.

Heretofore, several processes have been proposed for the chlorination of xylenols. For example, Japanese Patent Publication No. 40882/70 discloses a process for chlorinating xylenols in a hot aqueous hydrochloric acid solution, using cupric chloride as a chlorinating agent, and Japanese Patent Publication No. 35344/74 discloses a process for chlorinating xylenols likewise in a hot aqueous hydrochloric acid solution, using cupric chloride as a catalyst, while introducing a chlorine gas to the reaction system. It is shown that these two processes can produce p-chloroxylenols with considerably high selectivities. However, these processes still have various problems to be solved in their application on an industrial scale. That is, there are problems as to materials of construction due to the use of hot hydrochloric acid, safety due to use of oxygen for regenerating cupric chloride, increase in economical burden due to the complicatedness of the step for regenerating cupric chloride, troubles of formation of tarry matters from raw materials due to the use of chlorine gas, etc.

Generally, it is said that the selectivity to p-chloro isomers or o-chloro isomers resulting from the chlorination of xylenols depends upon their substituents on one hand, and kinds of chlorinating agents to be used in the chlorination on the other hand. For example, in the chlorination of 3,5-xylenol with molecular chlorine, a ratio of the product p-chloro-3,5-xylenol to the product o-chloro-3,5-xylenol, which will be hereinafter referred to as "P/O ratio", amounts to only 1.5, whereas P/O ratio is increased to 6 with sulfuryl chloride known as a milder chlorinating agent. Thus, a process for selectively producing p-chloroxylenols by chlorinating xylenols with sulfuryl chlorides, thereby increasing the P/O ratios, has been preferably employed so far.

On the other hand, in the chlorination of o-cresol in the adjacent art field, it has been proposed to use a catalyst in addition to sulfuryl chloride as the chlorinating agent to further increase the P/O ratio. For example, British Patent Specification No. 948601 discloses a process for chlorinating o-cresol using a halide of aluminum, iron, tin or zinc, above all, their chloride, as the catalyst, and German Pat. No. 1203275 discloses a process for chlorinating o-cresol, using metallic iron, tin, zinc or aluminum, or their alcoholate.

The present inventors made extensive studies on a process for chlorinating xylenols industrially advantageously with a higher selectivity in higher yield on the basis of these facts, and found that it was possible to provide an industrial scale process having a very high selectivity to p-chloro isomers in very high yield and less problems as to the safety and handling by carrying out the chlorination in the presence of at least one of said metal chlorides as a chlorinating catalyst, and at least one of sulfur compounds at the same time. The present invention is based on the foregoing finding. That is, it is an unexpected fact that selectitivies to p-chloro isomers and yields from xylenols can be considerably increased, irrespectively of the kinds of xylenols, by employing the metal chloride and the sulfur compound at the same time, for the sulfur compound itself has rather an action to lower the selectivity, and the metal chloride itself cannot always contribute to the increase in selectivity to the p-chloro isomers, but is effective only for increasing the yield, depending upon the kinds of xylenols.

The catalyst used in the present invention is metal chlorides usually employed as a catalyst in the ionic type chlorination reaction. Examples of the metal chloride include ferric chloride, aluminum chloride, antimony trichloride, antimony pentachloride, tellurium chloride, stannic chloride, titanium tetrachloride, bismuth trichloride, mercuric chloride and zinc chloride.

The sulfur compound to be used together in the present invention includes organic sulfur compounds such as thiophenes and their derivatives, for example, thiophene, 3-methylthiophene and tetrahydrothiopene; aliphatic mercaptans having 1 to 15 carbon atoms, for example, methylmercaptan, ethylmercaptan, n-butylmercaptan, t-butylmercaptan, hexylmercaptan, and dodecylmercaptan; sulfides, for example, dimethyl sulfide, dimethyl disulfide, diisobutyl sulfide, vinyl sulfide and benzyl sulfide; dimethyl sulfoxide; carbon bisulfide, thiourea, thioglycolic acid, L-cysteine; L-cystine, and inorganic sulfur compounds such as sulfuric acid, sodium thiosulfate, thionyl chloride, and antimony sulfide.

In the present invention, it is necessary to use 0.01 to 10% by weight of at least one of said metal chlorides as a catalyst, on the basis of the weight of xylenols to be chlorinated, and the remarkable effect of the present invention is attained by using 0.0001 to 1% by weight, preferably 0.01 to 0.1% by weight, of at least one of said organic or inorganic sulfur compounds as a promoter at the same time, on the basis of the weight of xylenols.

In the case of less than 0.01% by weight of the metal chloride, the catalyst effect is low, whereas in the case of more than 10% by weight, yield of unpreferable dichloro isomers is increased, resulting in reduction in the yield of the desired monochloro isomers, particularly, p-chloroxylenol.

In the case of 0.001% by weight or more of the sulfur compound as the promoter, the addition effect becomes remarkable, increasing the yield of p-chloro isomers and maintaining a high P/O ratio, whereas in the case of more than 1% by weight, the yield of di-chloro isomers is rather increased, and consequently p-chloroxylenol is decreased lowering the P/O ratio. Preferable amount of the sulfur compound to be added is 0.01 to 0.1% by weight, on the basis of the weight of xylenols.

The xylenols to be chlorinated in the present invention include 2,3-xylenol, 2,5-xylenol, 2,6-xylenol, 3,5- xylenol, and their derivatives, irrespective of kinds of their isomers or kinds of derivatives obtained from the isomers. Above all, the present invention is most suitable for the chlorination of para positions of 3,5-xylenol, which is of an industrial significance.

In the chlorination according to the present invention, any of a chlorine gas, phosphorus pentachloride, sulfuryl chloride and sulfur chloride can be also used as the chlorinating agent. Especially when an approximately theoretical amount of sulfuryl chloride is used on the basis of the xylenols, the chlorination proceeds mildly, suppressing production of dichloroxylenols, etc. as by-products. Thus, more remarkable catalytic effect can be obtained thereby.

The present process for chlorination can be carried out, irrespectively of the presence of a solvent, but it is usually desirable to carry out the present process after the xylenols have been dissolved in any of solvents for chlorination, including chlorinated hydrocarbons such as carbon tetrachloride, trichloroethylene, perchloroethylene, and dichlorobenzene. That is, since some of xylenols has a higher melting point, a higher temperature is inevitably required for the chlorination in the liquid state without any solvent. Thus, by the use of the solvent, the chlorination can be carried out at a low temperature with the remarkable effect of the catalyst and the sulfur compound in the present invention. In other words, the use of the solvent also has a further effect of preventing the formation of tarry matters due to the reaction at a high temperature. The amount of the solvent is not especially restricted in the present invention, but it is usually desirable to use the solvent in such an amount as to completely dissolve the raw material xylenols.

Further advantage of using the solvent obtained in the most cases in the present invention is deposition and precipitation of only p-chloroxylenols from the solution owing to differences in solubilities, and the resulting simple separation by filtering only the precipitate p-chloroxylenols. Since the precipitate p-chloroxylenols are crystallized out of the solution, the substantially same effect as that of recrystallization can be obtained with an advantage of unnecessitating further step of purification.

The present process can be carried out without any special restriction to reaction conditions only by adding the predetermined amounts of the metal chloride as the catalyst and the sulfur compound as the promoters to the xylenols, and then introducing the desired chlorinating agent into the reaction system. Usually, it is advantageous to use the chlorinated hydrocarbon as the solvent, and carry out the chlorination in the solvent. In that case, the chlorination reaction is carried out at such a temperature as to keep the raw material xylenols, the catalyst and the sulfur compound in a liquid state, preferably 5° to 45° C., whereby purification and separation of p-chloroxylenols as a main product can be facilitated. Said chlorination reaction can be carried out usually under the atmospheric pressure without any trouble, but also can be carried out either under an elevated pressure or under a reduced pressure, if desired. The present process can be also carried out batch-wise or continuously.

According to the present invention, p-chloroxylenols can be obtained with high selectivities in high yields, and furthermore since no oxygen is used in contrast to said prior art, it is not necessary to take an explosion problem of the raw material xylenols into account. Furthermore, since no hot hydrochloric acid is used, it is not necessary to take a special safety precaution or use of special acid-resistant materials of construction of apparatus into account. The fact that the present process can be carried out approximately at room temperature is a great advantage in handling. Furthermore, no complicated step for the necessary regeneration as required when cupric chloride is used as the chlorinating agent is needed in the present invention. Thus, the present invention can provide an economical process.

Now, the present invention will be described in detail, referring to Examples.

EXAMPLE 1

Into a four-necked separable flask having a capacity of 1,000 ml, provided with a stirrer, a thermometer, a nozzle for introducing a chlorinating agent, and a reflux cooler were charged 600 g of tetrachloroethylene and 122 g (1 mole) of 3,5-xylenol. Then, 0.2 g (0.16% by weight on the basis of 3,5-xylenol) of anhydrous ferric chloride as a catalyst and 0.6 g (1.9% by weight on the basis of 3,5-xylenol) of thiophene as a promoter were added thereto, and the resulting mixture was sufficiently stirred and subjected to reaction while adding 135 g of sulfuryl chloride as a chlorinating agent drop by drop at a rate of 0.8 g/minute and keeping the temperature at 20° C. In the course of reaction, reaction product p-chloro-3,5-xylenol was started to deposit. After the completion of dropwise addition of sulfuryl chloride, the temperature of the reaction solution was elevated to 65° C. by means of water bath to remove the dissolved acidic gas, and completely dissolve the reaction product once into the tetrachloroethylene at the same time. A portion of the resulting solution was sampled and analyzed by gas-chromatography. As a result, it was found that the solution had the following composition excluding the solvent tetrachloroethylene and the catalyst thiophene:

| | |
|---|---|
| p-chloro-3,5-xylenol | 89.4% by mole |
| o-chloro-3,5-xylenol | 8.5% by mole |
| 2,4-dichloro-3,5-xylenol | 0.4% by mole |
| 3,5-xylenol | 0.7% by mole |
| P/O ratio = 10.5 | |

The reaction solution was slowly cooled to 15° C. with stirring, and deposited crystals were filtered and dried, whereby 119 g of white crystals was obtained. The crystals had the following composition according to gas chromatographic analysis.

| | |
|---|---|
| p-chloro-3,5-xylenol | 99.7% by weight |
| 3,5-xylenol | 0.3% by weight |

COMPARATIVE EXAMPLE 1

The chlorination reaction was carried out under the same conditions as in Example 1, except that only 0.8 g of anhydrous ferric chloride as the catalyst was used in the absence of the promoter. The resulting reaction solution had the following composition:

| | |
|---|---|
| p-chloro-3,5-xylenol | 81.0% by mole |
| o-chloro-3,5-xylenol | 14.9% by mole |
| 2,4-dichloro-3,5-xylenol | 2.0% by mole |
| 3,5-xylenol | 1.5% by mole |
| Others | 0.6% by mole |

P/O ratio = 5.43

106 g of crystals was obtained by the same crystallization operation as in Example 1 with an yield of 68.0%.

EXAMPLE 2

The chlorination reaction was carried out under the same conditions as in Example 1, using the same reaction apparatus as in Example 1, except that 600 g of carbon tetrachloride as the solvent, 1.55 g of anhydrous aluminum chloride as the catalyst and 0.01 g of dodecylmercaptan as the promoter were used. The resulting reaction solution had the following composition:

| | |
|---|---|
| p-chloro-3,5-xylenol | 89.3% by mole |
| o-chloro-3,5-xylenol | 7.0% by mole |
| 2,4-dichloro-3,5-xylenol | 2.1% by mole |
| 3,5-xylenol | 1.0% by mole |
| Others | 0.6% by mole |
| P/O ratio = 12.7 | |

COMPARATIVE EXAMPLE 2

The chlorination reaction was carried out under the same conditions as in Example 1, using the same reaction apparatus as in Example 1, except that only 1.6 g of anhydrous aluminum chloride was used as the catalyst. The resulting reaction solution had the following composition:

| | |
|---|---|
| p-chloro-3,5-xylenol | 83.0% by mole |
| o-chloro-3,5-xylenol | 12.0% by mole |
| 2,4-dichloro-3,5-xylenol | 3.0% by mole |
| 3,5-xylenol | 1.0% by mole |
| Others | 0.8% by mole |
| P/O ratio = 6.80 | |

EXAMPLE 3

The chlorination reaction was carried out under the same conditions as in Example 1, but changing only the kind of the promoters, as shown in Table 1, and the resulting reaction solutions had the compositions as shown in Table 2.

TABLE 1

| Run No. | Metal chloride as catalyst | | Sulfur compound as promoter | |
|---|---|---|---|---|
| 3-1 | Anhydrous ferric chloride | 1 g | Dodecylmercaptan | 0.02 g |
| 3-2 | Anhydrous ferric chloride | " | 98% Sulfuric acid | 0.8 g |
| 3-3 | Anhydrous ferric chloride | " | t-Butylmercaptan | 0.3 g |

TABLE 2

| | Composition of reaction solution (% by mole) | | | | | |
|---|---|---|---|---|---|---|
| Run No. | p-Chloro isomer | o-Chloro isomer | Dichloro isomer | 3,5-xylenol | Others | P/O |
| 3-1 | 90.3 | 6.4 | 0.2 | 2.8 | 0.3 | 14.1 |
| 3-2 | 86.7 | 10.0 | 1.8 | 0.8 | 0.7 | 8.7 |
| 3-3 | 88.8 | 8.3 | 1.3 | 1.0 | 0.6 | 10.7 |

EXAMPLE 4

The chlorination reaction was carried out under the same conditions as in Example 1, using the same reaction apparatus as in Example 1, except that 600 g of o-dichlorobenzene as the solvent, 8.5 g of titanium tetrachloride as the catalyst, and 0.02 g of dodecylmercaptane as the promoter were used, and the resulting reaction solution had the following composition:

| | |
|---|---|
| p-chloro isomer | 91.5% by mole |
| o-chloro isomer | 6.3% by mole |
| dichloro isomer | 1.3% by mole |
| 3,5-xylenol | 0.3% by mole |
| Others | 0.6% by mole |
| P/O ratio = 14.4 | |

What is claimed is:

1. In a process for chlorinating xylenols which comprises employing as a catalyst 0.01 to 10% by weight of at least one metal chloride selected from the group consisting of ferric chloride, aluminum chloride, titanium tetrachloride, and antimony pentachloride based upon the weight of the xylenols and introducing sulfuryl chloride as a chlorinating agent to the reaction system, wherein the improvement comprises employing in the reaction system 0.001 to 1% by weight based upon the weight of the xylenols of at least one saturated aliphatic mercaptan containing only carbon and hydrogen in the alkyl group and having 1 to 15 carbon atoms and carrying out the chlorination in the presence of a chlorinated hydrocarbon solvent.

2. A process according to claim 1 wherein said aliphatic mercaptan is butylmercaptan or dodecylmercaptan.

3. A process according to claim 1 wherein said xylenol is 3,5-xylenol.

4. A process according to claim 1 wherein the chlorination is carried out at 5° to 45° C.

5. A process according to claim 1 wherein said chlorinated hydrocarbon solvent is carbon tetrachloride, tetrachloroethylene or o-dichlorobenzene.

6. The process of claim 1 wherein said chlorinating hydrocarbon solvent is selected from the group consisting of carbon tetrachloride, trichloroethylene, perchloroethylene, dichlorobenzene, and mixtures thereof.

7. The process of claim 1 wherein said mercaptan is selected from the group consisting of methylmercaptan, ethylmercaptan, n-butylmercaptan, t-butylmercaptan, hexylmercaptan, dodecylmercaptan, and mixtures thereof.

* * * * *